US007559490B2

(12) United States Patent
Rappin

(10) Patent No.: US 7,559,490 B2
(45) Date of Patent: Jul. 14, 2009

(54) NOZZLE ASSEMBLY

(75) Inventor: Craig Rappin, Long Grove, IL (US)

(73) Assignee: Roll LLC, Cary, IL (US)

(*) Notice: Subject to any disclaimer, the term of this patent is extended or adjusted under 35 U.S.C. 154(b) by 372 days.

(21) Appl. No.: 11/532,555

(22) Filed: Sep. 18, 2006

(65) Prior Publication Data

US 2007/0029407 A1 Feb. 8, 2007

Related U.S. Application Data

(63) Continuation-in-part of application No. 11/461,925, filed on Aug. 2, 2006, which is a continuation-in-part of application No. 10/974,400, filed on Oct. 26, 2004, now Pat. No. 7,213,773, which is a continuation-in-part of application No. 10/924,522, filed on Aug. 24, 2004, now abandoned.

(51) Int. Cl.

| | |
|---|---|
| ***A62C 15/00*** | (2006.01) |
| ***A62C 13/62*** | (2006.01) |
| ***B05B 9/08*** | (2006.01) |
| ***B05B 15/00*** | (2006.01) |
| ***B05B 7/30*** | (2006.01) |
| ***A61M 11/02*** | (2006.01) |
| ***F23D 11/16*** | (2006.01) |

(52) U.S. Cl. ....................... 239/154; 239/289; 239/340; 239/369; 239/419

(58) Field of Classification Search ................. 239/152, 239/154, 289, 304, 369, 419, 340
See application file for complete search history.

(56) References Cited

U.S. PATENT DOCUMENTS 1,475,957 A 12/1923 Lemons
1,947,743 A 2/1934 Schoeneck (Continued)

FOREIGN PATENT DOCUMENTS

EP 0837738 4/1998

(Continued)

OTHER PUBLICATIONS

Non-Final Office Action issued on Dec. 23, 2008 for U.S. Appl. No. 11/456,654.

(Continued)

*Primary Examiner*—Len Tran
*Assistant Examiner*—Ryan Reis
(74) *Attorney, Agent, or Firm*—Neal, Gerber & Eisenberg LLP

(57) ABSTRACT

A liquid spray nozzle assembly for an outlet pipe of an air blower, the nozzle assembly includes an outer annular member adapted to be secured to the outlet pipe, an inner member radially spaced from and secured to the outer member to define air flow passages, the inner member having a central opening and a lower surface with vanes extending therefrom; and a supply pipe extending into the central opening such that the air flowing through the central opening will act to shear the liquid exiting the supply pipe against the edge of the opening to break up the liquid into droplets that will be carried along in a dispersed pattern with the air flowing between the outer annular member and the inner member.

13 Claims, 10 Drawing Sheets

U.S. PATENT DOCUMENTS

| | | | | | |
|---|---|---|---|---|---|
| 1,986,407 | A | | 1/1935 | Parker | |
| 2,708,596 | A | | 5/1955 | Weller | |
| 2,738,226 | A | | 3/1956 | Bals | |
| 3,776,459 | A | | 12/1973 | Bonvicini | |
| 4,089,441 | A | | 5/1978 | Cole et al. | |
| 4,111,364 | A | | 9/1978 | Schroeder | |
| 4,244,062 | A | | 1/1981 | Corsette | |
| 4,474,327 | A | | 10/1984 | Mattson et al. | |
| 4,476,515 | A | | 10/1984 | Coffee | |
| D280,125 | S | | 8/1985 | Butterfield et al. | |
| 4,597,203 | A | | 7/1986 | Middleton | |
| 4,688,643 | A | | 8/1987 | Carter et al. | |
| D293,929 | S | | 1/1988 | Verhees | |
| D294,287 | S | | 2/1988 | Verhees | |
| 4,768,714 | A | | 9/1988 | Luchsinger | |
| 5,176,303 | A | | 1/1993 | Franke | |
| 5,195,208 | A | | 3/1993 | Yamami et al. | |
| 5,240,186 | A | * | 8/1993 | Dobbins et al. | 239/690.1 |
| 5,303,866 | A | | 4/1994 | Hawks, Jr. | |
| 5,385,106 | A | | 1/1995 | Langshaw | |
| 5,429,278 | A | | 7/1995 | Sansalone | |
| 5,562,248 | A | | 10/1996 | Khalifka | |
| 5,636,791 | A | | 6/1997 | Leer | |
| 5,671,884 | A | | 9/1997 | Restive | |
| 5,678,766 | A | | 10/1997 | Peck et al. | |
| 5,727,707 | A | | 3/1998 | Wickland et al. | |
| 5,752,661 | A | | 5/1998 | Lewis | |
| 5,813,088 | A | | 9/1998 | Wagner et al. | |
| D408,495 | S | | 4/1999 | Adams | |
| 5,947,384 | A | | 9/1999 | McCauley | |
| 5,988,414 | A | | 11/1999 | Schwartz et al. | |
| 6,003,199 | A | | 12/1999 | Shaffer | |
| 6,092,260 | A | | 7/2000 | Kai | |
| 6,185,917 | B1 | | 2/2001 | Goudes | |
| D439,636 | S | | 3/2001 | Hamilton | |
| 6,206,300 | B1 | | 3/2001 | Roudebush et al. | |
| 6,223,827 | B1 | | 5/2001 | Zuev et al. | |
| 6,371,388 | B2 | * | 4/2002 | Utter et al. | 239/419 |
| 6,409,097 | B1 | * | 6/2002 | McCauley | 239/289 |
| 6,575,695 | B1 | | 6/2003 | Miyamoto | |
| 6,776,133 | B2 | | 8/2004 | Tezuka et al. | |
| 6,793,563 | B2 | | 9/2004 | Daniel | |
| 6,834,413 | B2 | | 12/2004 | Sanders et al. | |
| 6,837,447 | B1 | | 1/2005 | Clark | |
| 6,889,773 | B2 | * | 5/2005 | Hanratty | 169/14 |
| 7,007,826 | B2 | | 3/2006 | Shapanus et al. | |
| 7,021,391 | B2 | * | 4/2006 | Schasteen | 169/14 |
| 7,055,213 | B2 | | 6/2006 | Iida et al. | |
| 7,065,944 | B1 | | 6/2006 | Steele | |
| 7,073,734 | B2 | | 7/2006 | Dorendorf et al. | |
| 7,086,616 | B2 | | 8/2006 | Murphy et al. | |
| D542,376 | S | | 5/2007 | Blete et al. | |
| 7,213,773 | B1 | | 5/2007 | Rappin | |
| 7,234,653 | B2 | | 6/2007 | Powell et al. | |
| D558,300 | S | | 12/2007 | Rappin | |
| 7,374,111 | B2 | | 5/2008 | Joseph et al. | |
| 7,437,796 | B2 | | 10/2008 | Rappin | |
| 2001/0041316 | A1 | | 11/2001 | Haynes et al. | |
| 2004/0123991 | A1 | | 7/2004 | Hanratty | |
| 2004/0135004 | A1 | | 7/2004 | Fex | |
| 2005/0006400 | A1 | | 1/2005 | Shapanus et al. | |
| 2007/0119972 | A1 | | 5/2007 | Fex | |
| 2007/0170187 | A1 | | 7/2007 | Tharp et al. | |
| 2008/0011708 | A1 | | 1/2008 | Rappin | |
| 2008/0163450 | A1 | | 7/2008 | Disanto | |
| 2008/0172826 | A1 | | 7/2008 | Rappin | |

FOREIGN PATENT DOCUMENTS

| | | |
|---|---|---|
| GB | 2095966 | 10/1982 |
| JP | 2001193697 | 7/2001 |

OTHER PUBLICATIONS

The International Search Report and The Written Opinion of the International Searching Authority mailed on Apr. 2, 2009 with regard to PCT/US2008/069936.

Non-Final office Action issued on May 1, 2008 for U.S. Appl. No. 11/461,925, filed Aug. 2, 2006.

Final Office Action issued on Nov. 20, 2008 for U.S. Appl. No. 11/461,925, filed Aug. 2, 2006.

* cited by examiner

NOZZLE ASSEMBLY

This application is a continuation-in-part of application Ser. No. 11/461,925 filed on Aug. 2, 2006, which is a continuation-in-part application of application Ser. No. 10/974,400 filed Oct. 26, 2004 which is a continuation-in-part of application Ser. No. 10/924,522 filed Aug. 19, 2004.

FIELD OF THE INVENTION

The invention relates to a nozzle assembly used for distributing liquid yard treatments such as pesticides and herbicides, and the same used with a portable blower for distributing such liquid treatments.

BACKGROUND OF THE INVENTION

Various devices have been known for the application of liquid materials for lawns and for controlling insects. Typically, a prior art device would utilize a portable leaf blower or other fan propelled misting devices to spray the liquid treatment. However, most of these systems are somewhat flawed for various reasons as explained herein.

For example, U.S. Pat. No. 6,793,563 discloses a particulate blaster assembly with a vacuum generating assembly secured to the air directing tube near the inlet to the air blower. The particulates when introduced into the air directing tube will have to travel approximately the entire length of the tube. Eventually this type of device can cause a buildup of material along the internal perimeter of the tube and can prevent the device from being used for other types of treatments (i.e. the same tube could not be used for spraying a weed/grass control substance and then used to spray a pesticide).

Other types of systems such as U.S. Patent Application Publication No. 2004/0135004 require the device to have its own power supply means to blow the treatment out of the reservoir. These types of systems add unnecessary weight to the system especially if the user is carrying both the device and another lawn care motorized device such as an air blower or weed trimmer.

While the prior art does include devices that release the liquid treatment at the end of the blower tube, these devices introduce the liquid treatment at the circumference of an exit port of the blower tube. For example, U.S. Pat. No. 5,947,384 shows a yard blower with a blower tube and a liquid yard treatment reservoir secured to the blower tube and having a feeding tube positioned at the end of the blower tube. These devices do not introduce the liquid treatment within the airflow. This can be a problem because as the airflow leaves the blower tube, the airflow is extremely turbulent and typically expands in all directions. The treatment may thus never enter the main stream of the airflow and thus may be constantly blown out at a single direction and carried by a specific portion of the airflow; rather than being carried or mixed with the entire or major portion of the airflow.

While the prior art has certain suitable characteristics, they do not provide a simple, easy to use, and reliable apparatus for dispensing a liquid yard treatment, as provided for herein. There is thus a need for a compact, portable, highly effective nozzle system that can be used with readily available equipment to conveniently spray liquid yard treatments in an effective manner that does not require the liquid material to be introduced at some point within the middle of the blower tube or require a separate power supply. The present invention also provides for a more effective manner of introducing the liquid yard treatment at the exit of the blower tube.

SUMMARY OF THE INVENTION

In accordance with an embodiment of the present invention there is provided an apparatus for distributing liquid yard treatment. The apparatus includes a portable blower for creating airflow through a blower tube. The blower tube has an exit end through which the airflow exits. The apparatus further includes a reservoir containing a liquid yard treatment. An end cap is secured to the exit end of the blower tube. The end cap has a inlet end through which the airflow enters and has an exit end through which the airflow exits. A nozzle is centrally positioned within the end cap and has a substantially centrally positioned aperture. The apparatus further includes a feeding tube with one end in fluid communication with the reservoir and with another end positioned about the aperture, such that liquid flows from the reservoir to the nozzle and exits the nozzle about the aperture such that the liquid is substantially centrally positioned in the airflow.

The apparatus may also include at least one clip positioned externally along the blower tube for securing the feeding tube to the blower tube. The apparatus may also have a coiled region defined along the feeding tube that is also positioned near the reservoir.

Additionally, the apparatus may include a valve mechanism positioned along a portion of the feeding tube that is along the blower tube. The valve mechanism has an open position to allow fluid to flow there through and has a closed position. The apparatus may further include another valve mechanism along the feeding tube. This valve mechanism has two separate interconnecting portions that when detached separates the feeding tube into two sections that are considered non-connected. When the interconnecting portions of the valve mechanism are detached the flow of liquid is stopped and when attached the valve mechanism is automatically opened and the two sections of the feeding tube are connected in fluid communication such that the flow of liquid is permitted.

The apparatus may also include a pair of openings defined on the end cap that align with a pair of openings defined on the blower tube. A pair of pins is provided that are separatly inserted into the aligned openings to secure the end cap to the blower tube.

In another embodiment, a system for distributing liquid yard treatment for use with a portable blower that creates airflow through a blower tube is provided. The system includes a reservoir containing a liquid yard treatment, a nozzle secured to an exit end of the blower tube, and a feeding tube having one end in fluid communication with the reservoir and having another end in fluid communication with the nozzle. The nozzle has a fluid inlet for communication with one end of the feeding tube. The nozzle also has an exit aperture centrally positioned on the nozzle through which the liquid yard treatment exits. The nozzle further includes openings around the aperture through which the airflow exits, such that the liquid is substantially centrally positioned within the airflow.

In yet another embodiment, a liquid spray nozzle assembly for an outlet pipe of an air blower is disclosed. The nozzle assembly includes an outer annular member adapted to be secured to the outlet pipe. The nozzle assembly further includes an inner member radially spaced from and secured to the outer member to define air flow passages. The inner member has a central opening and a lower surface with vanes extending therefrom. The vanes of which may be arcuately shaped to aid in directly airflow through the central opening. A supply pipe of liquid extends into the central opening whereby the air flowing through the central opening will act to shear the liquid exiting the supply pipe against the edge of the tapered opening to break up the liquid into droplets that will be carried along in a dispersed pattern with the air flowing between the outer annular member and the inner member.

The nozzle assembly may further include an inner member that is concentrically shaped. The inner member may also have an upper surface that is outwardly tapered towards the central opening. In addition, the inner member may be secured to the outer annular member by a plurality of support members. The support members may include a ledge positioned to receive a clip defined by the supply pipe such that the supply pipe is attached to the support members.

The outer annular member may also include a protrusion to define a channel for receiving a section of the supply pipe for the intake of the liquid. Furthermore, the outer annular member may include a pair of extending members, each having a means for securing the outer annular member to the outlet pipe. Such securing means may be a pair of dog ears with apertures that align with apertures on the outlet pipe.

Numerous other advantages and features of the invention will become readily apparent from the following detailed description of the invention and the embodiments thereof, from the claims, and from the accompanying drawings.

BRIEF DESCRIPTION OF THE DRAWINGS

A fuller understanding of the foregoing may be had by reference to the accompanying drawings, wherein.

DETAILED DESCRIPTION OF THE EMBODIMENTS

Figure 1:
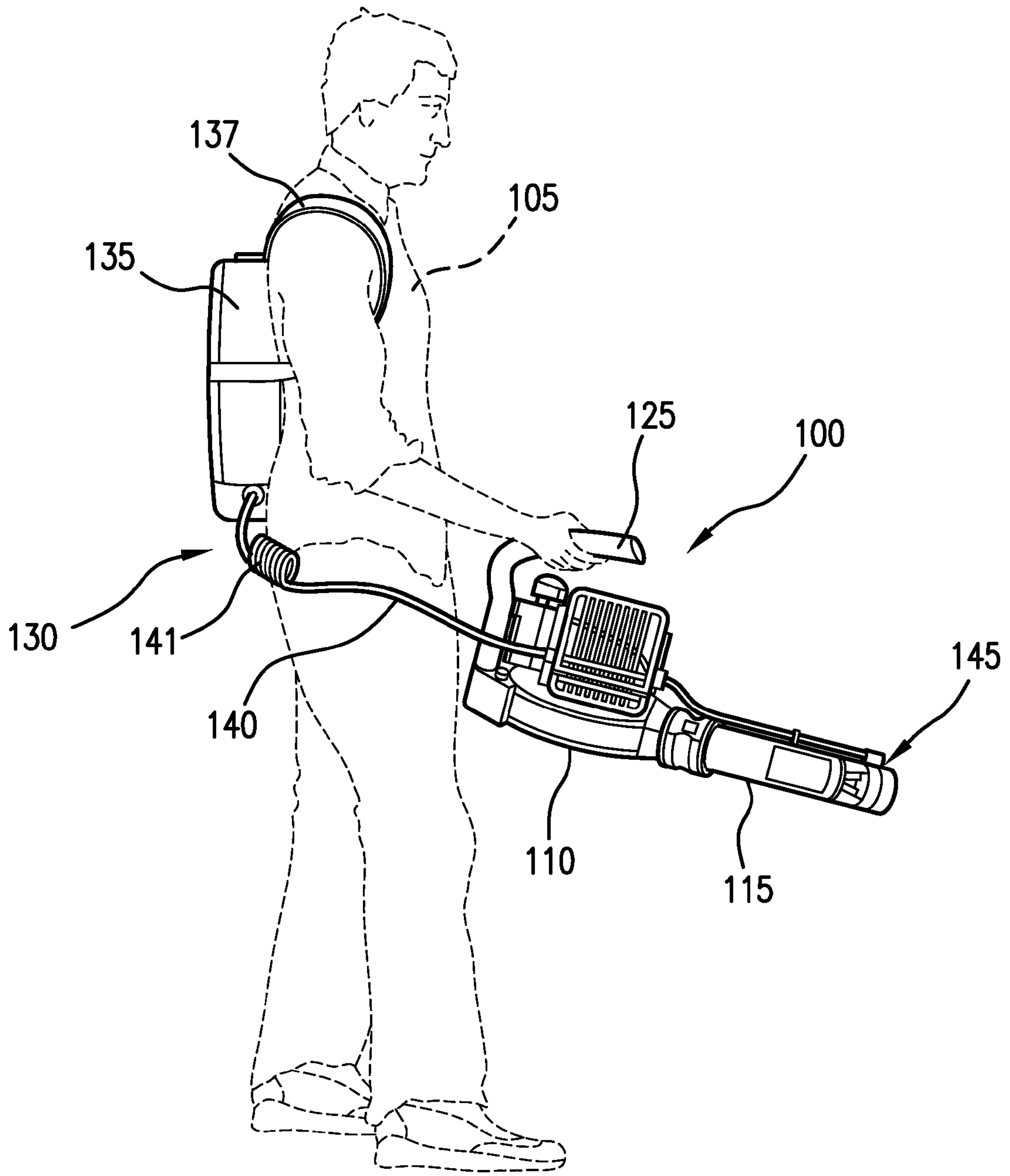
FIG. 1 is a perspective view of a system for distributing a liquid yard treatment in accordance with an embodiment of the present invention.

While the invention is susceptible to embodiments in many different forms, there are shown in the drawings and will be described herein, in detail, the preferred embodiments of the present invention. It should be understood, however, that the present disclosure is to be considered an exemplification of the principles of the invention and is not intended to limit the spirit or scope of the invention and/or claims of the embodiments illustrated.

Referring first to FIG. 1 there is illustrated a system for distributing a liquid yard treatment, generally designated as 100. The liquid yard treatment may consist of any type of pesticide or herbicide and may be mixed with water. The system 100 includes a portable blower 110 which generates an airflow that is distributed through a blower tube 115. The blower 110 typically includes a handle 125 which can be held by the hand of a user 105. Blower tube 115 includes an end 120 through which airflow exits the blower tube. A liquid treatment distribution system 130 is provided and connected to the blower 110 for introducing the treatment into the existing airflow.

As shown in FIG. 2 the liquid treatment distribution system 130 includes a reservoir 135 that contains the treatment. The treatment flows from the reservoir 135 through a feeding tube 140 to a nozzle assembly 145 that is secured to the end 120 of the blower tube 115. The reservoir 135 is carried on the back of the user 105 by the use of straps 137 (shown in FIG. 1). In this particular embodiment the liquid treatment distribution system 130 uses gravity to flow the liquid treatment from the reservoir 135. (However, other systems such as suction or siphon systems may be employed.)

Figure 2A:
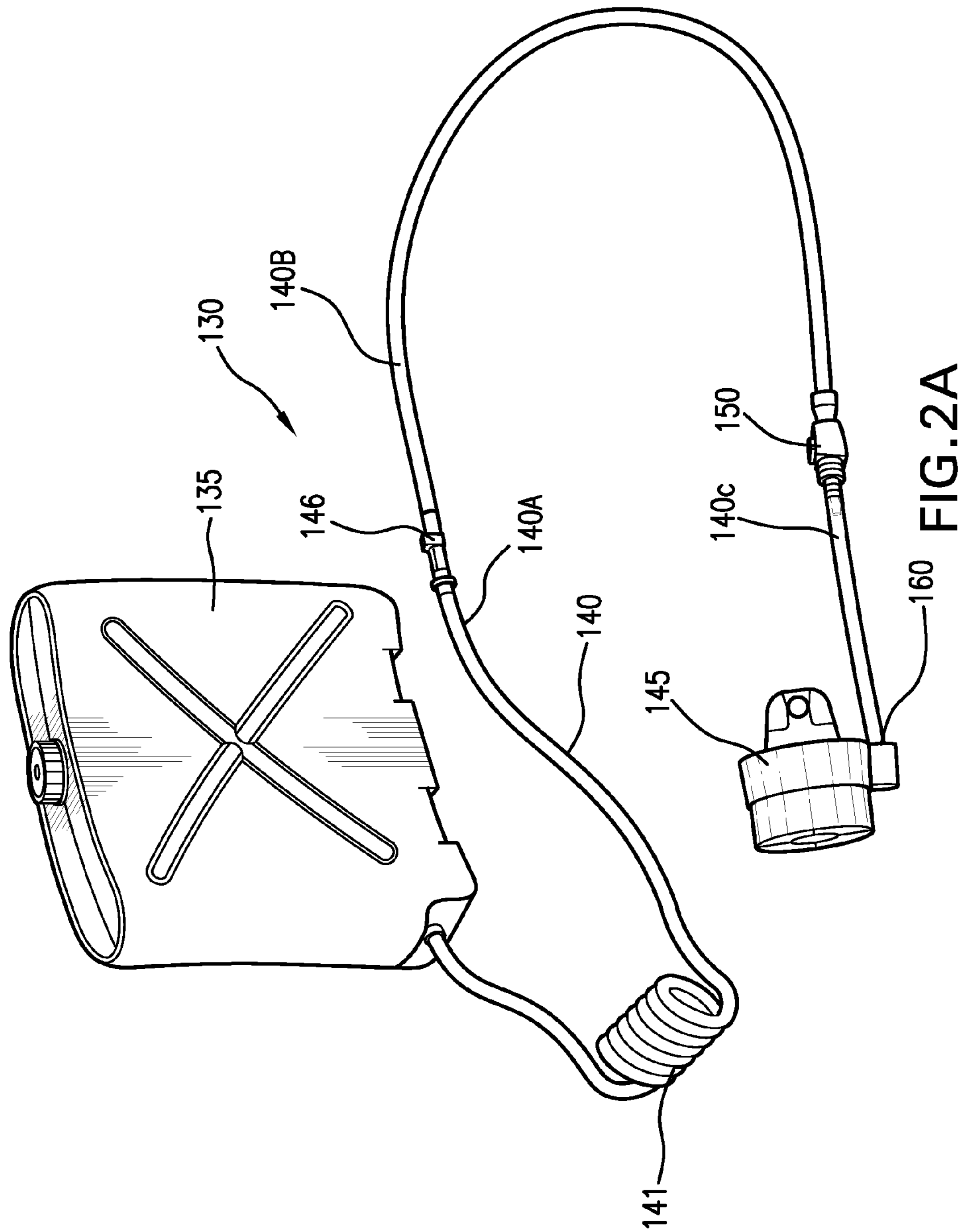
FIG. 2*a* is a perspective view of a liquid treatment distribution system in accordance with an embodiment of the present invention.
Figure 3:
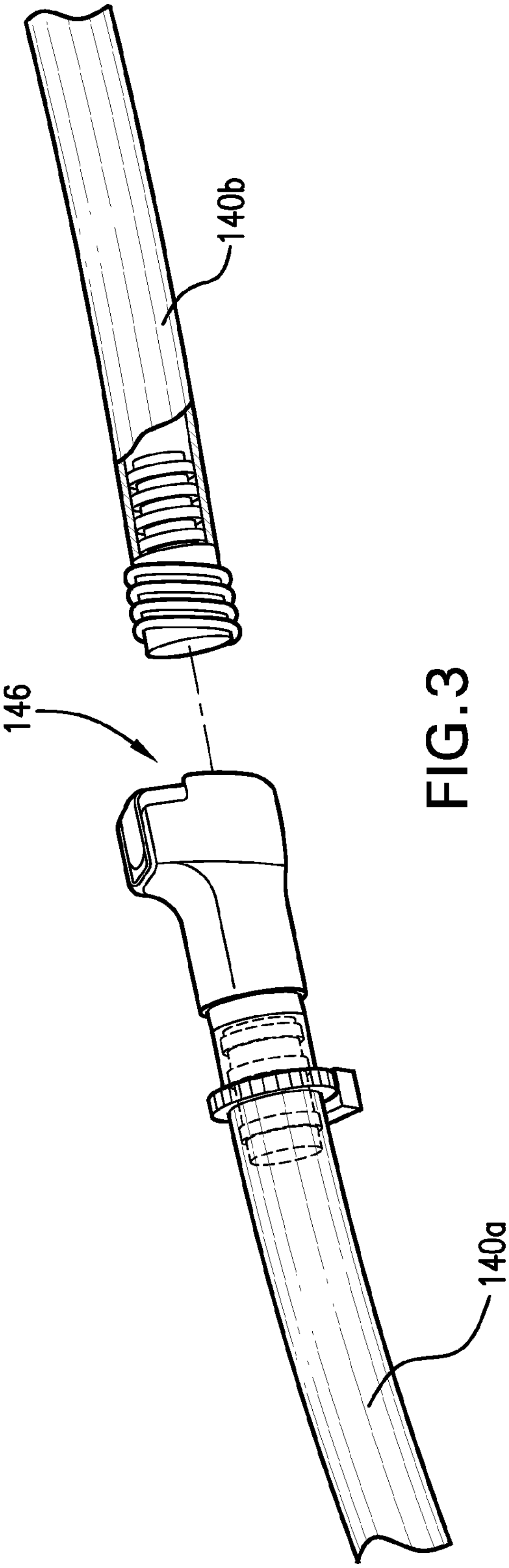
FIG. 3 is a perspective view of a disconnect valve mechanism used along the feeding tube on the liquid treatment distribution system in accordance with an embodiment of the present invention.

The feeding tube 140 includes a coiled region 141 towards the reservoir 135 this helps to maintain the feeding tube 140 taut such that excess feeding tube is not dragged and does not get in the way. The feeding tube 140 further includes one or more valves that aid in shutting off the flow of the treatment. The flow may need to be turned off for various reasons, such as, the user may wish to switch back and forth from regular yard work to treating the yard, or when finished. The embodiment shown in FIG. 2A illustrates the use of two valves. A first valve 146 is capable of separating the feeding tube 140, illustrated in FIG. 3, into two sections 140*a* and 140*b*. This provides for an easy means of cleaning or refilling the reservoir 135 without carrying the entire system 100 or without carrying the entire liquid treatment distribution system 130. The feeding tube 140 also includes a second valve 150 positioned at a point along the blower tube 115. While the second valve 150 also separates the feeding tube 140 into two sections 140*b* and 140*c*, the second valve 150 may not be a full release of the two sections 140*b* and 140*c*. Thus when the second valve 150 is pressed, the two sections 140*b* and 140*c* will stay connected to each other but the fluid communication between the two sections will shut off. This would permit the flow of treatment to be cut off but still allow the user to easily reconnect the flow with a single hand. Both types of valves are well known in the valve industry. Moreover, the present invention is not intended to be limited by the valves described herein as different valves may be used without deviating from the spirit and scope of the invention.

As mentioned above, the feeding tube 140 connects the reservoir 135 to the nozzle assembly 145. As illustrated in FIGS. 2A, 2B, 4 and 5, an end 160 of the feeding tube 140 is secured to an L shaped connector 165 that is in fluid communication to a tubular section 170. The tubular section 170 includes a protruding exit member 175 along the length of the tubular section 170 and includes a pair of clips or supports 180. The treatment will thus flow from the feeding tube 140 into the tubular section 170 and exit through the protruding exit member 175.

Figure 4:
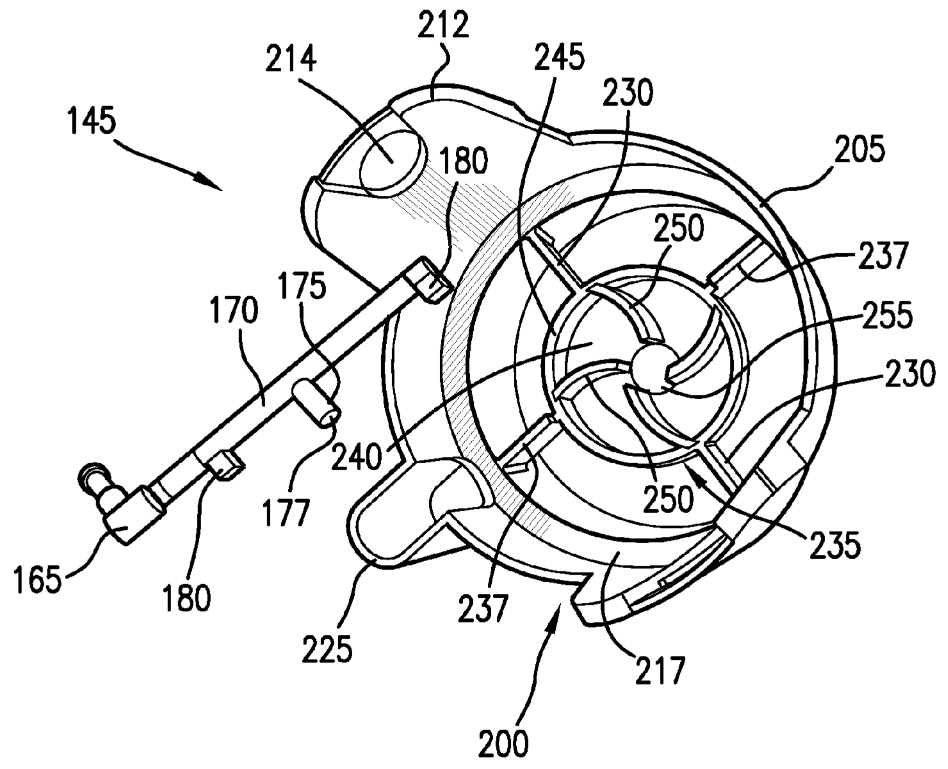
FIG. 4 is a rear perspective view of a nozzle assembly in accordance with an embodiment of the present invention illustrating a tube used to direct the treatment to the center of an end cap.
Figure 6:
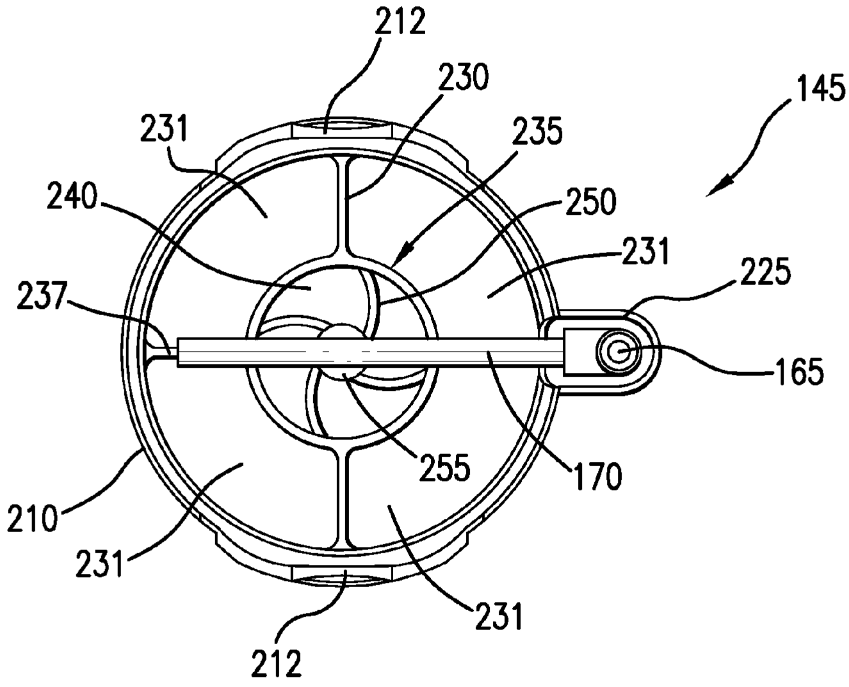
FIG. 6 is a top view of FIG. 4.
Figure 5:
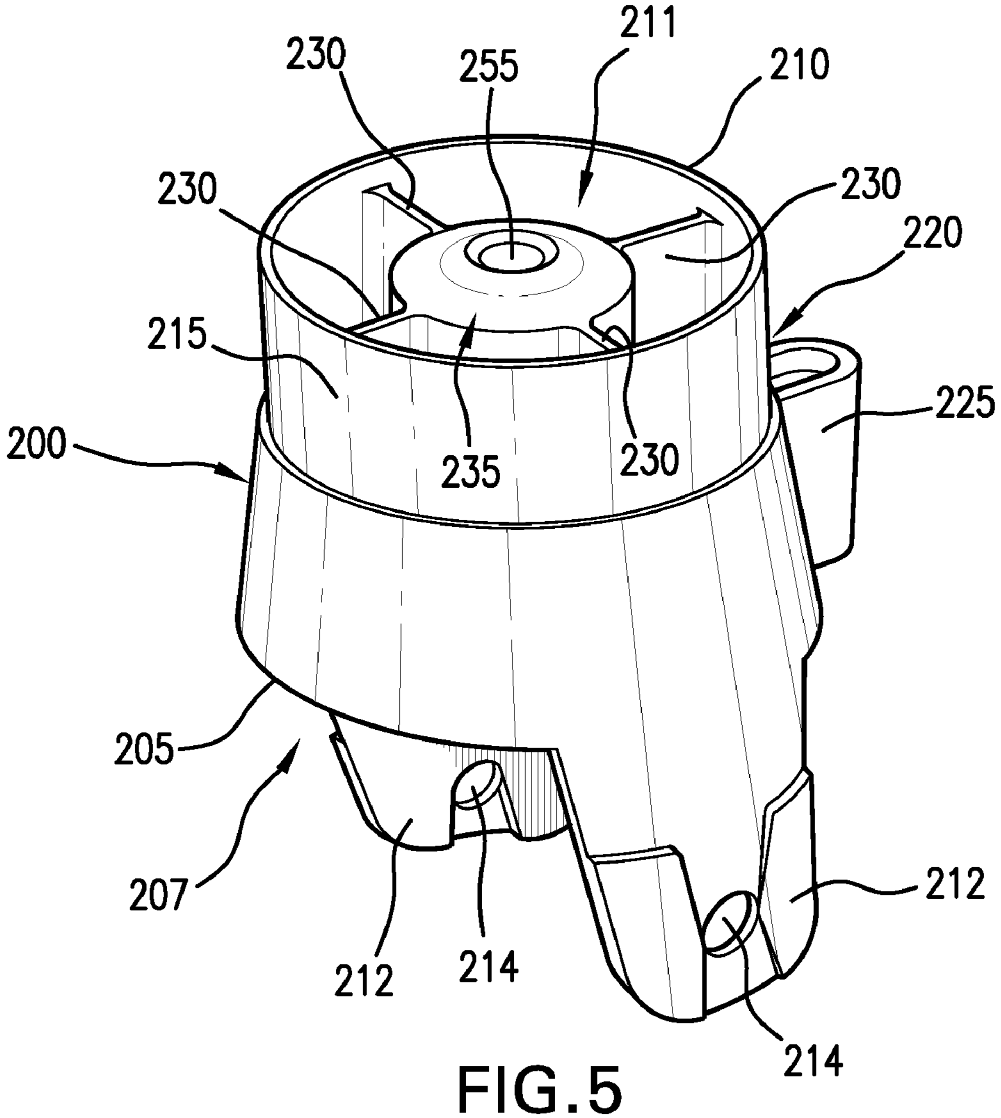
FIG. 5 top side perspective view of FIG. 4.
Figure 7:
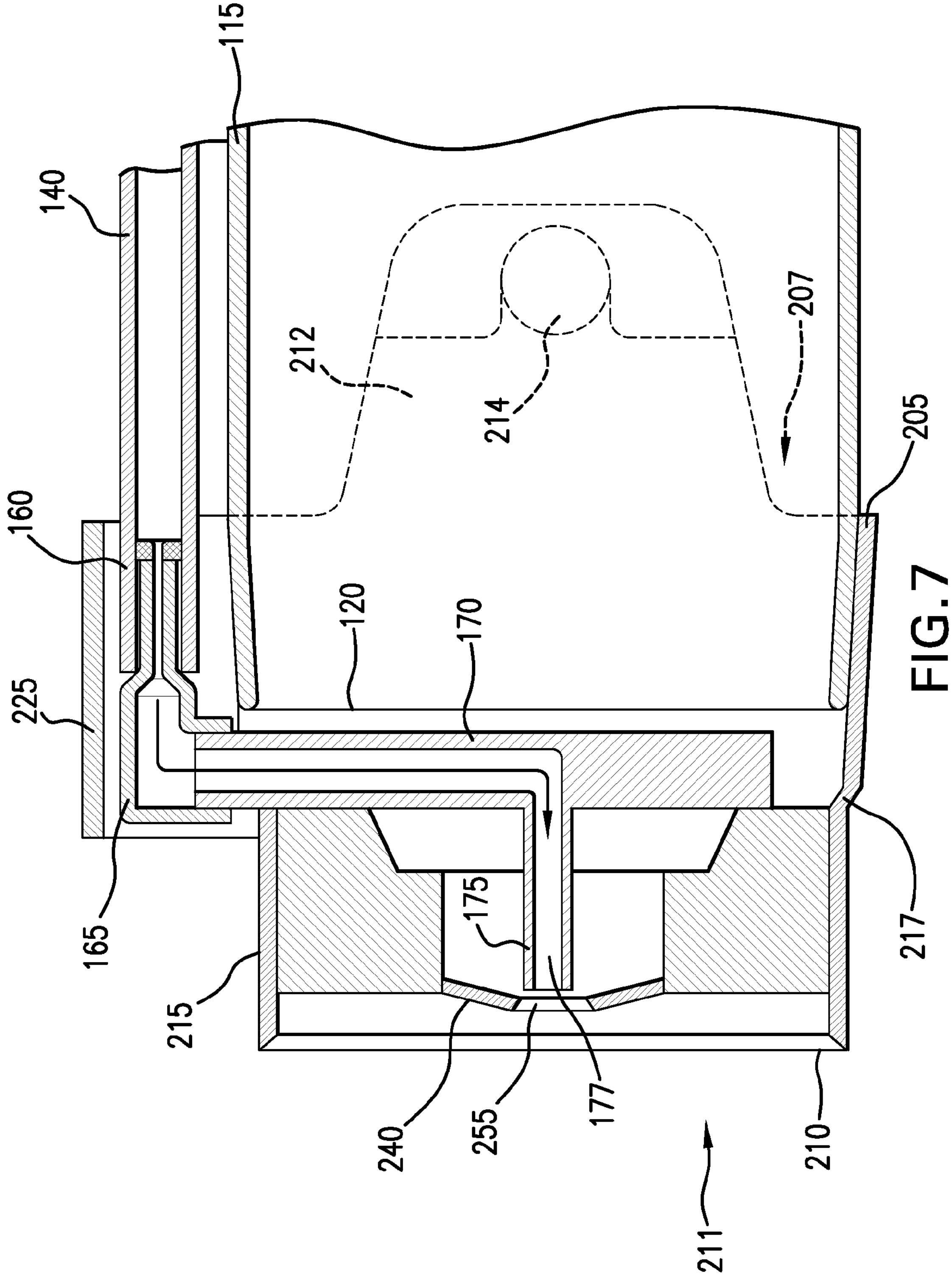
FIG. 7 is a cross section view of the nozzle assembly shown connected to the blower tube and feeding tube.

Best shown in FIGS. 4, 6, and 7, the nozzle assembly 145 includes an end cap 200. The end cap 200 includes a first end 205 about an entrance region 207 that is secured to the blower tube 115 and includes a second end 210 about an exit region 211. The first end 205 and the second end 210 are connected through a wall 215. A pair of dog ears 212 extends away from the first end 205 and includes openings 214 such that the end cap 200 may be secured to the blower tube 115.

Figure 2B:
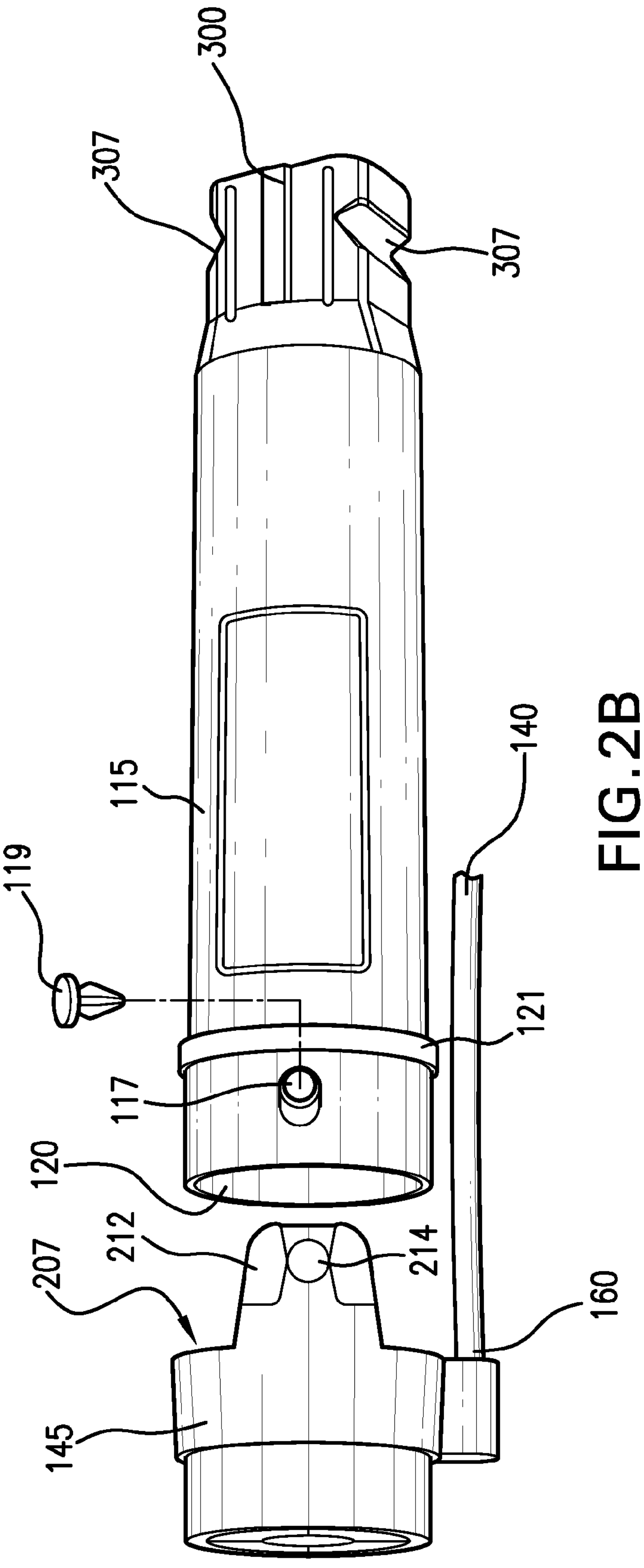
FIG. 2*b* is a perspective view of a nozzle assembly and a blow tube.

As shown in FIG. 2B, to connect the nozzle assembly 145 to the blower tube 115, the openings 214 defined on the dog ears 212 on the end cap 200 are aligned with openings 117 on the blower tube 115. Pins 119 are then inserted to lock the two together. The blower tube 115 may further include a outwardly extending ledge 121 that may help to prevent end cap 200 being pushed to far onto the end of the blower tube 115 prior to aligning the openings and inserting the pins 119. The end cap 200 may also include a ledge 217 (shown in FIGS. 4 and 7) extending internally which would prevent the end cap 200 from being pushed too far onto the end of the blower tube 115 as the internal ledge 217 would come into contact with the end 120 of the blower tube 115.

Referring back to FIGS. 4 and 5, protruding from the exterior of the wall 215 is a section 220, which includes a channel 225 sized to receive the L shaped connector 165. The channel 225 protrudes outwardly from the wall 215 such that the end 160 of the feeding tube 140 can attach to the tubular section 170 and the treatment may flow into the end cap 200.

Internally, the end cap 200 includes supports 230 that extend radially inward from the wall 215 towards the center of the end cap 200. Some of the supports 230 also include a ledge 237 (explained in greater detail below). The supports 230 attach to a nozzle 235 centered within the exit region 210. The supports 230 are separated by opened regions 231 through which the airflow may exit the end cap 200 around the nozzle 235.

The nozzle 235 has a top portion 240 that terminates into a skirt 245 that extends back into the end cap 200. The supports 230 are secured to the skirt 245. A plurality of blades 250 are secured to the inside portion of the skirt 245 and to the inside portion of the top portion 240. The top portion 240 further includes an aperture 255. Alternatively, the top portion 240 may be angled such that it is diverging towards the aperture 255. The blades 250 may also be angled and/or curved to help direct the flow of air towards the aperture 255.

When assembled (FIGS. 6 and 7), the supports 180 on the tubular section 170 mate with the ledges 237 defined on some of the supports 230. The tubular section 170 is then aligned such that the connector 165 is positioned in the channel 225 and the protruding exit member 175 is positioned at the aperture 255 in the top portion 240. The end 177 of the protruding exit member 175 may be flushed with the aperture 255, recessed as illustrated, or even protruding from the aperture. Therefore, the protruding exit member 175 is positioned along the tubular section 170 at a point that is substantially centered or along the symmetrical axis of the nozzle assembly 145.

Figure 8:
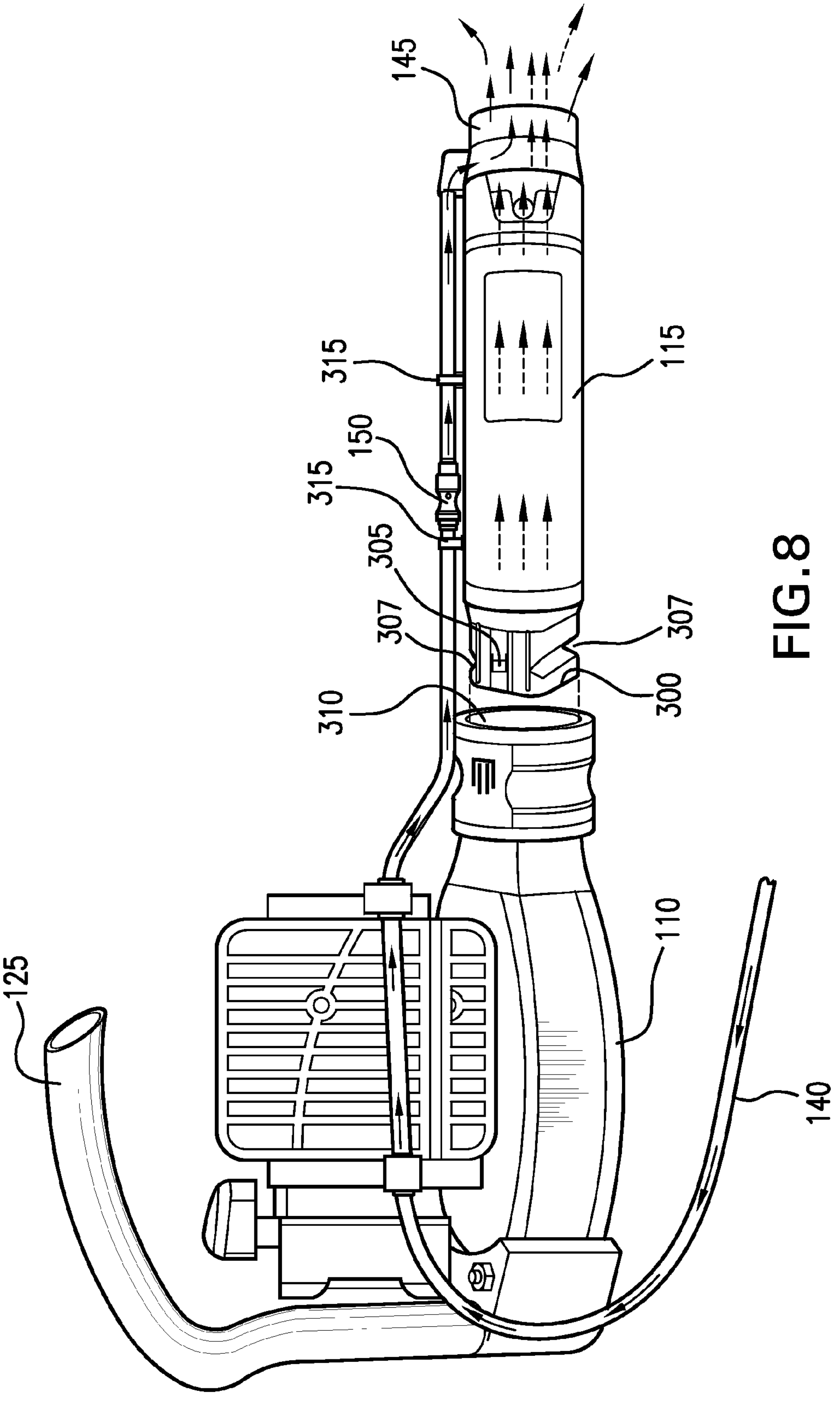
FIG. 8 is a perspective view of a portable blower and feeding tube from the liquid treatment distribution system further illustrating the blower tube disconnected from the air exit of the portable blower.

Illustrated in FIG. 8, the blower tube 115 is secured at one end 300 to the blower exit 310 on the portable blower 100. One means of connection would include detents 305 on the end 300 of the blower tube 115 that are secured to corresponding protruding locks (not shown) in the blower exit 310. Grooves 307 on the end 300 of the blower tube 115 may also be included to help guide or lock the blower tube 115 in place. The blower tube 115 also includes clips 315 to secure the feeding tube 140 thereto. This eliminates any problems caused by dangling tubes.

Figure 9:
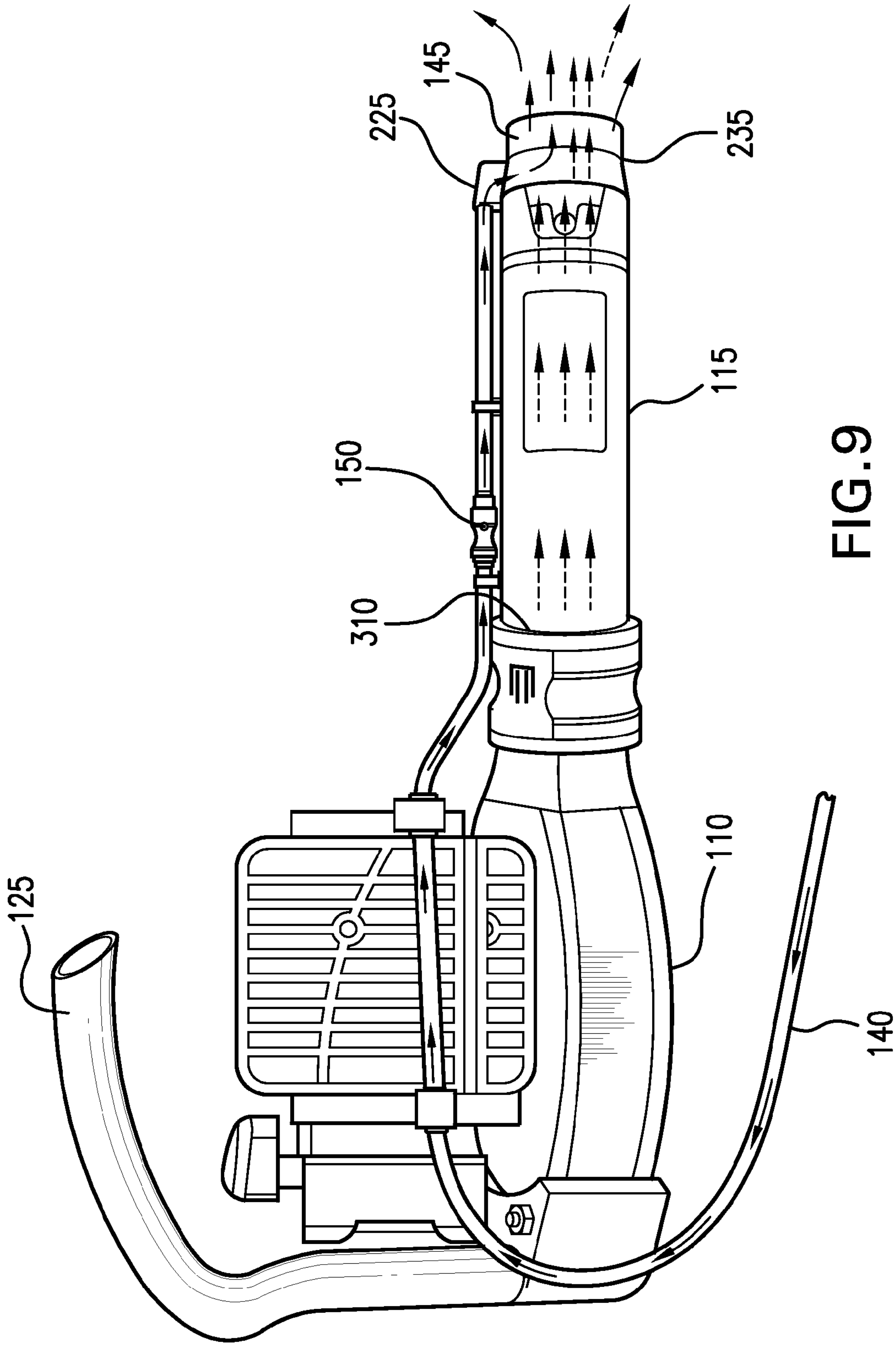
FIG. 9 is a perspective view of FIG. 8 illustrating the blower tube connected to the portable blower.

Referring now also to FIG. 9, once assembled, the portable blower 100 can be activated to create a flow of air. The second valve mechanism 150 can be opened to allow the fluid to continue its flow into the nozzle assembly 145. The treatment will then be introduced into the center of the airflow (rather than along the circumference). The airflow traveling through the nozzle 235 will become turbulent as it is directed by the blades and exits the aperture 255 to mix with the treatment. A portion of the airflow will also exit around the nozzle 235 through the exit regions 210 to keep the turbulent mixture of air and treatment centered as well as blown out a significant distance from the exit region 211.

Figure 10:
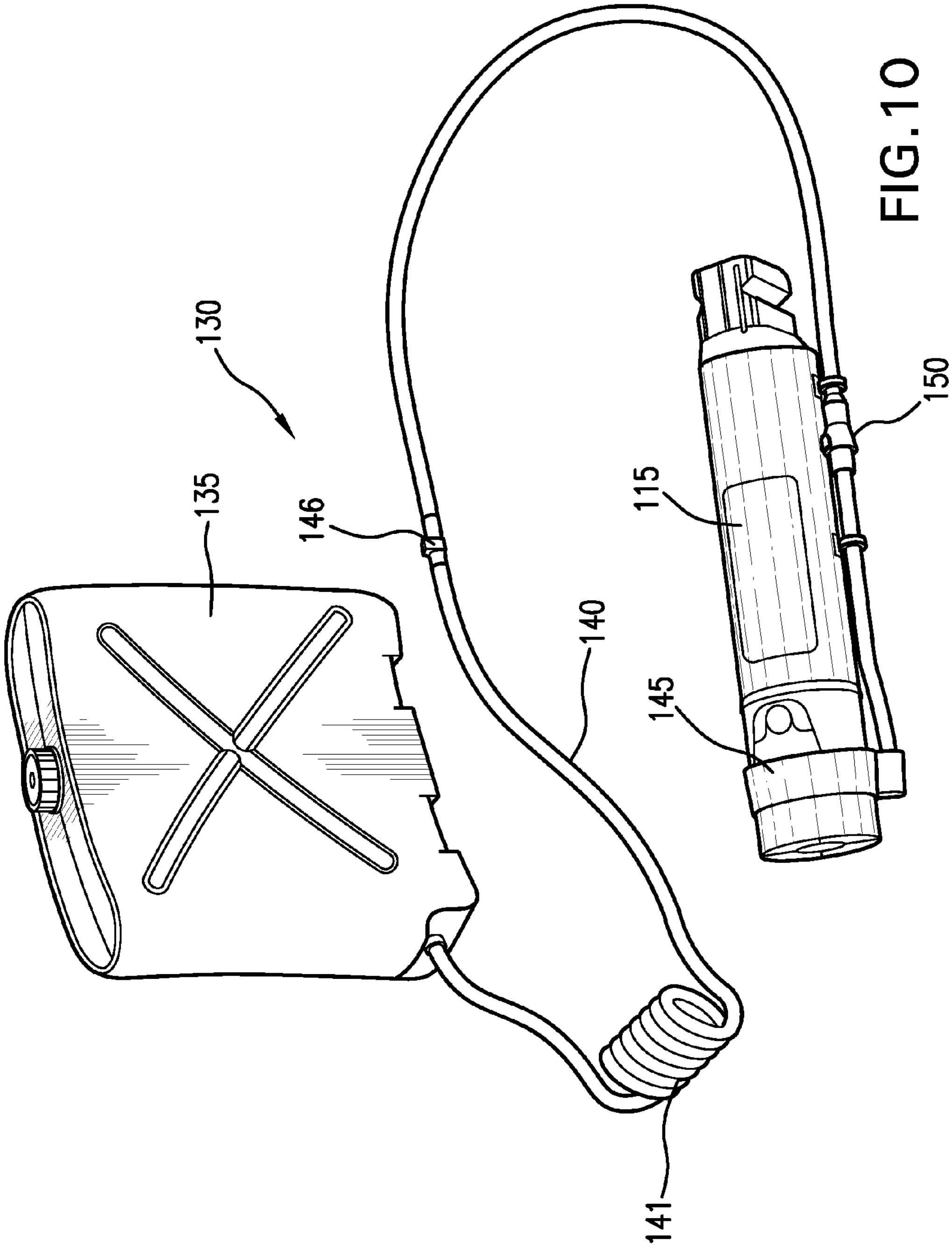
FIG. 10 is a perspective view of a liquid treatment distribution system with a blower tube connected to the nozzle assembly.

While the above description may refer to the blower tube 115 as being part of the portable blower 110, it is possible to retro fit a typical portable blower 110 with a liquid treatment distribution system 130 in accordance with the present invention. In those instances, a blower tube that is initially provided in the typical portable blower 100 is replaced with blower tube 115 described herein above. In those embodiments (illustrated in FIG. 10), the blower tube 115 becomes part of a kit 300 used to allow a user to convert a portable blower 110 to a system which includes a liquid treatment distribution system 130.

It should be further stated the specific information shown in the drawings but not specifically mentioned above may be ascertained and read into the specification by virtue of a simple study of the drawings. Moreover, the invention is also not necessarily limited by the drawings or the specification as structural and functional equivalents may be contemplated and incorporated into the invention without departing from the spirit and scope of the novel concept of the invention. It is to be understood that no limitation with respect to the specific embodiments illustrated herein is intended or should be inferred. It is, of course, intended to cover by the appended claims all such modifications as fall within the scope of the claims.

I claim:

1. A liquid spray nozzle assembly for an outlet pipe of an air blower, the nozzle assembly comprising:

an outer annular member adapted to be secured to the outlet pipe;

an inner member radially spaced from and secured to said outer annular member by a plurality of support members to define air flow passages, the inner member having a central opening and a lower surface with vanes extending therefrom; and a supply pipe extending into said central opening whereby air flowing through said central opening will act to shear liquid exiting the supply pipe against an edge of the central opening to break up the liquid into droplets that will be carried along in a dispersed pattern by the air flowing between the outer annular member and the inner member;

wherein at least one of the support members includes a ledge positioned to receive a clip defined by the supply pipe such that the supply pipe is attached to said at least one support member.

2. The assembly of claim 1, wherein the inner member is concentric to said outer member.

3. The assembly of claim 1, wherein the inner member further includes an upper surface that is outwardly tapered towards the central opening.

4. The assembly of claim 1, wherein the outer annular member includes a protrusion to define a channel for receiving a section of the supply pipe for intake of said liquid.

5. The assembly of claim 1, wherein the vanes are arcuate shaped.

6. A liquid disbursement end cap for use with a blower tube of an air blower, the end cap comprising:

an outer member having a means for being secured to said blower tube;

an inner member centrally positioned within the outer member and secured thereto by at least one support member to define airflow openings between the outer member and the inner member for exiting airflow, the inner member having a substantially centrally positioned aperture; and a conduit having an inlet for receiving a liquid and an outlet positioned near the centrally positioned aperture for releasing the liquid centrally within the exiting airflow;

wherein at least one support member includes a ledge for positioning a clip defined by the conduit such that a portion of the conduit is aligned with the at least one support member.

7. The end cap of claim 6, wherein the inner member includes a lower surface having a plurality of vanes extending therefrom to further direct airflow through the centrally positioned aperture.

8. The end cap of claim 7, wherein each vane is arcuate shaped.

9. The end cap of claim 6, wherein the inner member includes an outer surface that is tapered towards the centrally positioned aperture.

10. The end cap of claim 6, wherein the outer member includes a protrusion, the protrusion having a channel defined therein for receiving the inlet of the conduit.

11. The end cap of claim 6, wherein the inner member is concentric to said outer member.

12. The end cap of claim 6, wherein the outer member is annularly shaped.

13. A liquid spray nozzle assembly for an outlet pipe of an air blower, the nozzle assembly comprising:

an outer annular member adapted to be secured to the outlet pipe;

an inner concentric member radially spaced from and secured to said outer member by a plurality of support members to define air flow passages, the inner concentric member having an upper surface with a central tapered opening defined therein and a lower surface with vanes extending therefrom that are arcuately shaped towards said central tapered opening; and a supply pipe extending into said central tapered opening whereby air flowing through said central tapered opening will act to shear liquid exiting the supply pipe against an edge of the central tapered opening to break up the liquid into droplets that will be carried along in a dispersed pattern by the air flowing between the outer annular member and the inner concentric member;

wherein at least one of the support members includes a ledge positioned to receive a clip defined by the supply pipe such that the supply pipe is attached to said at least one support member.

* * * * *